United States Patent
Shah et al.

(10) Patent No.: US 10,167,522 B2
(45) Date of Patent: Jan. 1, 2019

(54) NUCLEIC ACID PROBES AND METHODS FOR DETECTING PLASMODIUM KNOWLESI

(71) Applicant: ID-FISH TECHNOLOGY, INC., Santa Clara, CA (US)

(72) Inventors: Jyotsna S. Shah, Santa Clara, CA (US); Akhila Poruri, Fremont, CA (US); Olivia Mark, San Jose, CA (US)

(73) Assignee: ID-Fish Technology, Inc., Santa Clara, CA (US)

( * ) Notice: Subject to any disclaimer, the term of this patent is extended or adjusted under 35 U.S.C. 154(b) by 0 days.

(21) Appl. No.: 15/389,827

(22) Filed: Dec. 23, 2016

(65) Prior Publication Data

US 2018/0179599 A1  Jun. 28, 2018

(51) Int. Cl.
*C12Q 1/6893* (2018.01)

(52) U.S. Cl.
CPC ..... *C12Q 1/6893* (2013.01); *C12Q 2600/158* (2013.01)

(58) Field of Classification Search
CPC .................................................. C12Q 1/6893
See application file for complete search history.

(56) References Cited

U.S. PATENT DOCUMENTS

| 5,519,127 A | 5/1996 | Shah et al. |
| 5,629,156 A | 5/1997 | Shah et al. |
| 2016/0362753 A1 | 12/2016 | Shah et al. |

FOREIGN PATENT DOCUMENTS

| WO | WO 9947706 A1 * | 9/1999 | ........... C12Q 1/6874 |
| WO | 2016037142 A1 | 3/2016 | |

OTHER PUBLICATIONS

Babady, N.E. et al. Am. J. Trop. Med. Hyg. 81(3):516 (2009).*
Divis, P. et al. Malaria Journal 9:344 (2010).*
Lee, P.C. et al. Malaria Journal 14:28 (Jan. 2015).*
Lau. Y-L. et al. Am. J. Trop. Med. Hyg. 94(2):336 (2016; online Nov. 2015).*
Yusof, R. et al. Emerging Infectious Diseases 22(8):1371 (Aug. 2016).*
Singh, B. et al. Am. J. Trop. Med. Hyg. 60(4):687 (1999).*
Lucchi, N.W. et al. PLoS One 7(2):e31848 (Feb. 2012).*
Singh, B. et al. The Lancet 363(9414):1017 (Mar. 2004).*
Moyes, et al. "Defining the Geographical Range of the Plasmodium Knowlesi Reservoir" PLOS Neglected Tropical Diseases; Mar. 2014; vol. 8; Issue 3; e2780; pp. 1-13.
Yusof, et al. "High proportion of knowlesi malaria in recent malaria cases in Malaysia" Malaria Journal; 2014; vol. 13; Issue 168; pp. 1-9.
Singh, et al. "A large focus of naturally acquired Plasmodium knowlesi infections in human beings" The Lancet; Mar. 27, 2004; vol. 363; pp. 1017-1024.
Ramasamy "Zoonotic malaria—global overview and research and policy needs" Frontiers in Public Health; Aug. 2014; vol. 2; Article 123; pp. 1-7.
Shah, et al. "Fluorescene in Situ Hybridization (FISH) Assays for Diagnosing Malaria in Endemic Areas" PLOS One; Sep. 2, 2015; pp. 1-15.
Moon, et al. "Adaptation of the genetically tractable malaria pathogen Plasmodium knowlesi to continuous culture in human erythrocytes" PNAS; Jan. 8, 2013; vol. 110; No. 2; pp. 531-536.
Shah, et al. "Fluorescence in Situ Hybridization (FISH) for diagnosing malaria in endemic areas" 2016; Poster presentation at Anglia Ruskin University, Cambridge, England.
Chin, et al. "A Naturally Acquired Quotidian-Type Malaria in Man Transferable to Monkeys" Science; 1965; vol. 149; p. 865.
Shah et al "Dual color fluorescence in situ hybridization (FISH) assays for detecting Mycobacterium tuberculosis and Mycobacterium avium complexes and related pathogens in cultures" PLOS; Apr. 11, 2017; pp. 1-14.
GenBank KC581789.1 "Plasmodium knowlesi isolate MO48-7 small subunit ribosomal RNA gene, partial sequence" May 20, 2013; downloaded from internet at https://www.ncbi.nlm.nih.gov/nuccore/KC581789.1; 1 page.
Kawamoto, et al. "Sequence Variation in the 18S rRNA gene, a Target for PCR-Based Malaria Diagnosis, in Plasmodium ovale from Southern Vietnam" Journal of Clinical Microbiology; Sep. 1996; vol. 34; No. 9; pp. 2287-2289.

* cited by examiner

*Primary Examiner* — Diana B Johannsen
(74) *Attorney, Agent, or Firm* — Pierce Atwood LLP; Kevin M. Farrell; David J. Wilson

(57) ABSTRACT

This invention relates to novel nucleic acid probes and methods for detecting *Plasmodium knowlesi* parasites in a sample.

15 Claims, 3 Drawing Sheets
Specification includes a Sequence Listing.

NUCLEIC ACID PROBES AND METHODS FOR DETECTING PLASMODIUM KNOWLESI

SEQUENCE LISTING

The instant application contains a Sequence Listing which has been submitted electronically in ASCII format and is hereby incorporated by reference in its entirety. Said ASCII copy, created on Mar. 29, 2017, is named 0153-2011US01_SL.txt and is 1,390 bytes in size.

BACKGROUND OF THE INVENTION

Malaria is one of the most common infectious diseases and an enormous public-health problem. Determining the infectious species responsible for a malaria infection helps determine the course of treatment for the patient. The four common species of human malaria parasites, i.e., *Plasmodium falciparum, Plasmodium vivax, Plasmodium malariae* and *Plasmodium ovale*, that are transmitted between humans by anopheline mosquito vectors have an ancient zoonotic origin. Zoonotic malaria is currently a relatively neglected aspect of human malaria. Alterations in patterns of human settlements in the vicinity of forests, and deforestation, are increasing human proximity to primate malaria hosts in the tropics causing zoonotic malaria to become an emerging human health concern. Primate malaria parasites that are naturally transmitted by anopheline mosquito vectors to humans at the present time include the catarrhine monkey parasites *Plasmodium knowlesi* and *Plasmodium cynomolgi* in Southeast Asia, the platyrrhine monkey parasites *Plasmodium brasilianum* and *Plasmodium simium* in South America, and *Plasmodium vivax*-like parasites from apes in West Africa.

The clinical significance of *Plasmodium knowlesi* malaria is increasingly recognized in Southeast Asia after the initial discovery of a focus of human infections in the Kapit division of the Sarawak state in Malaysian Borneo, subsequently in peninsular Malaysia and then in other Southeast Asian countries. *Plasmodium knowlesi* is normally a parasite of *Macaca fascicularis* (the long-tailed or crab-eating macaque), *M. nemestrina* (the pig-tailed macaque), *Trachypithecus obscuras* (dusky leaf monkey or spectacled langur) and *Presbytis melalophus* (banded leaf monkey or brown langur).

*Plasmodium knowlesi* infections in humans are commonly misidentified as *P. malariae* and *P. falciparum* during routine microscopic examination of Giemsa stained blood smears because of morphological similarities between the blood stages. Therefore, the definitive identification of human infections caused by *P. knowlesi* presently relies on PCR-based techniques. The diagnosis of *P. knowlesi* malaria is important in a clinical context because its pathogenicity and drug treatment options can differ from the human malaria caused by *P. falciparum, P. malariae, P. ovale* and *P. vivax* that are also prevalent in the Southeast Asian region. Rapid immunochromatography-based diagnostic tests (RDTs) are being increasingly used worldwide to detect malaria but a reliable RDT for specifically detecting *P. knowlesi* is not yet available. PCR-based assays are sensitive enough to detect 1-5 parasites per μl of blood and able to discriminate between the different *Plasmodium* species that infect humans, including *P. knowlesi*. However PCR-based assays are relatively expensive, time consuming, and require specialized equipment. PCR-based techniques are therefore not suitable for routine diagnosis in typical peripheral and district-level diagnostic laboratories, but valuable for use in central reference laboratories in the *P. knowlesi*-endemic regions of Southeast Asia.

What is needed are reagents and methods for the rapid and accurate detection and discrimination of malaria causing *Plasmodium knowlesi*.

SUMMARY OF THE INVENTION

This invention relates to nucleic acid probes that detect and discriminate *Plasmodium knowlesi* parasites in, for example, hybridization assays. Accordingly, in a first aspect, the invention features nucleic acid fragments to be used as probes for detecting *Plasmodium* in a hybridization assay. The invention also includes probes (DNA, RNA and PNA) that can detect *P. knowlesi* and discriminate *P. knowlesi* from other *Plasmodium* sp. In the context of the present invention the term "discriminates between" (or similar terms) means that the probe binds to nucleic acid (e.g., RNA, DNA, rRNA [ribosomal RNA] or rDNA [ribosomal DNA]) from one species more favorably than other species.

The invention contemplates a method for detecting the presence of *Plasmodium knowlesi* in a sample. In this method, a sample is contacted with a nucleic acid fragment containing (i.e., "consisting of," "consisting essentially of" or "comprising") a sequence selected from, preferably a partial (e.g., at least five, at least ten, more preferably or most preferably at least fifteen consecutive nucleotides) or the entire sequence of a PK1 and/or PK2 and/or PK3 probe selected from or the partial or full-length complementary sequence thereof (or any combination thereof); under conditions that permit the nucleic acid fragment to hybridize to *Plasmodium* nucleic acid. Detection of the nucleic acid fragment bound to the *Plasmodium knowlesi* nucleic acid in the sample is used as an indication of the presence of *Plasmodium knowlesi* in the sample. Detection methods used with the present invention may be, for example, FISH assays, Dot-Blot assays, or any other suitable assay known to one of ordinary skill in the art.

The present invention contemplates a composition consisting of, consisting essentially of or comprising one or more of the probes of the present invention, i.e., PK1, PK2 and/or PK3, or a full length complement thereof. The present invention also contemplates a sequence selected from, preferably, at least five, at least ten, or most preferably at least fifteen consecutive nucleotides or the entire sequence of a PK1 and/or PK2 and/or PK3 probe or from the partial or full-length complementary sequence thereof (or any combination of probes thereof).

The present invention contemplates that the probes of the present invention are labeled by a suitable label or labels known to one of ordinary skill in the art. The present invention also contemplates in one embodiment that the label does not comprise or consist of the nucleotide(s) immediately adjacent 3' and/or 5' to the probe sequence or the complementary sequence thereof.

In any of the preceding embodiments, the probe or probes used may be of the entire nucleotide sequence as disclosed herein or the complementary strand thereof as well as the sequence or complementary sequence at least five, at least ten or at least fifteen contiguous nucleotides of the probes.

DETAILED DESCRIPTION OF THE INVENTION

Figure 1:
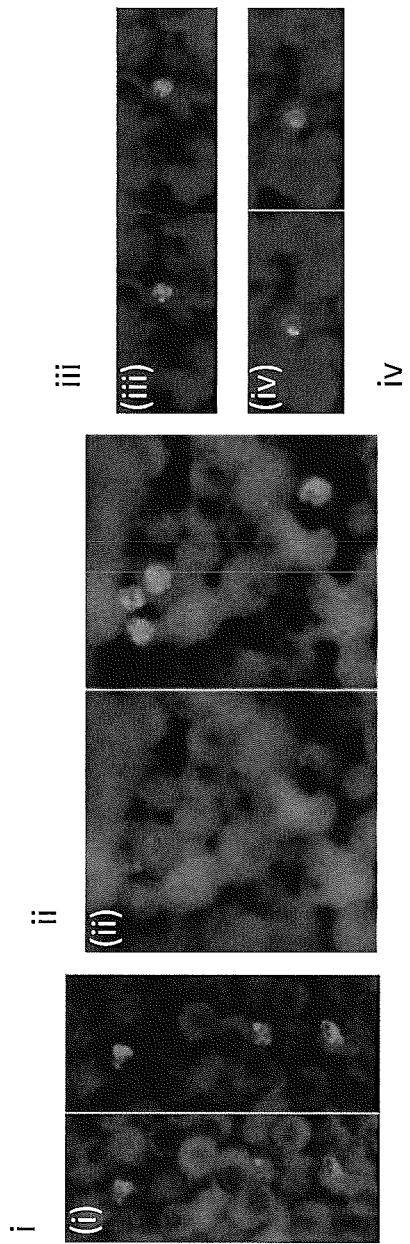
FIG. 1 (i-iv) shows photographs showing the fluorescence observed in the PK-FISH assay with the *P. knowlesi*-specific probe (green; left) and the *Plasmodium* genus-specific probe (orange; right) on monkey blood smears containing *P. knowlesi*. Fluorescence seen in a single microscope field at ×1000 magnification using the two different filters is shown in each set of paired photographs. The four sets of paired photographs are from four different fields (i)-(iv).

The invention features nucleic acid probes for detecting the *Plasmodium* parasite *P. knowlesi* in, for example, hybridization assays. The probes of the invention may be used in methods for detecting the presence of *P. knowlesi* in a biological sample. In these methods, a probe of the invention is contacted with a biological sample (e.g., whole blood, cerebrospinal fluid (CSF) or a tissue sample) in a hybridization assay and detection of the probe bound to the nucleic acid in the sample is used as an indication of the presence of *P. knowlesi* in the sample. Probes included in this invention are SEQ ID NO: 3, SEQ ID NO: 4 and SEQ ID NO: 5, or full length complementary sequences thereof. Probes suitable for use in the methods of the invention may also include sequences shorter than SEQ ID NOs: 3, 4 and 5. One of skill in the art would be able to determine a suitable probe shorter than the full-length probe or full-length complementary sequence without undue experimentation.

In a another aspect, the invention features a nucleic acid fragment containing a sequence selected from, preferably, at least five, more preferably at least ten or most preferably at least fifteen consecutive nucleotides or the entire sequence of one or more of probes designated PK1 [SEQ ID NO: 3], PK2 [SEQ ID NO: 4] and PK3 [SEQ ID NO: 5] or the partial or full-length complementary sequences thereof as well as methods of use of any or all of the sequences Further, any *Plasmodium knowlesi* sequence (e.g., a sequence encoding 58, 5.8S, 18S, or 28S ribosomal RNA) may be selected as a candidate sequence for the identification of probes. Preferred sequences are those that diverge from analogous sequences in non-human *Plasmodium* or other protozoan parasites like, for example, *Babesia* or *Thileria*, as determined by phylogenetic comparison. The nucleic acid probes of the invention are at least 5, 10 or 15 nucleotides in length and may contain deoxyribonucleotides (DNA probes), ribonucleotides (RNA probes), peptide nucleic acid (PNA probes) or combinations or modifications thereof. A peptide nucleic acid, as is known in the art, is a nucleic acid analog in which the sugar phosphate backbone of natural nucleic acid has been replaced by a synthetic peptide backbone usually formed from N-(2-amino-ethyl)-glycine units, resulting in an achiral and uncharged mimic. It is chemically stable and resistant to hydrolytic (enzymatic) cleavage and thus not expected to be degraded inside a living cell. PNA is capable of sequence-specific recognition of DNA and RNA obeying the Watson-Crick hydrogen bonding scheme, and the hybrid complexes exhibit extraordinary thermal stability and unique ionic strength effects.

The probes of the present invention may be single stranded or double stranded and may be prepared by any of a number of standard methods in the art. For example, the probes may be made by chemical synthesis, restriction endonuclease digestion of a vector (e.g., a plasmid containing a sequence corresponding to the probe), polymerase chain reaction (PCR) amplification, or in vitro transcription of a vector containing a sequence corresponding to the probe [see, e.g., Ausubel, et al., Current Protocols in Molecular Biology, Greene Publishing, New York, N.Y., 1994, incorporated herein by reference].

The probes may be labeled during or after synthesis. For example, labeled nucleotides containing, e.g., radioisotopes (e.g., p32, S35, or H3), biotin or digoxigenin may be incorporated into the probe during synthesis. Probes containing biotin are detected by the use of a secondary reagent such as avidin or streptavidin, which contains a detectable label such as a fluorochrome (e.g., fluorescein or rhodamine) or an enzyme (e.g., alkaline phosphatase or horseradish peroxidase). Similarly, probes containing digoxigenin may be detected by using a labeled antidigoxigenin antibody. Probes may also be labeled after synthesis by, e.g., nick translation or the use of T4 RNA ligase, poly(A) polymerase, terminal transferase or T4 polynucleotide kinase, in standard methods [see, e.g., Ausubel, et al., supra]. The probes may also contain modified nucleotides in order to increase the stability of the probe. For example, ribonucleotides containing 2'-0-alkyl groups on the ribose group may be used. The probes may also contain modifications that facilitate capture of the probe onto a solid support. For example, poly-dA or poly-deaza-guanosine tails may be added to the 3' ends of the probes, using terminal transferase, in order to facilitate probe binding to a solid support, e.g., poly-dT or poly-dC labeled magnetic particles. The present invention also contemplates in one embodiment that the label does not comprise or consist of the nucleotide(s) immediately adjacent 3' and/or 5' to the probe target sequence or the complementary sequence thereof Methods for identifying suitable *P. knowlesi* probes, including those specifically detailed in this application, include: (1) Preparing a nucleic acid fragment or polypeptide nucleic acid, PNA (i.e., a probe) corresponding to or complementary to a sequence of at least ten nucleotides of nucleic acid from *P. knowlesi* and (2) comparing the ability of the probe to detect all the *Plasmodium* species in a hybridization assay. Probes that hybridize to *P. knowlesi* more favorably than to other *Plasmodium* species are included in the invention.

*P. knowlesi* nucleic acid may be obtained from biological samples (such as whole blood, bone marrow, CSF) from infected individuals (human or other infected animal), using standard nucleic acid isolation methods in the art. *P. knowlesi* can also be obtained from culture. For example, DNA encoding *Plasmodium* ribosomal RNA may be obtained by PCR amplification of DNA prepared from a whole blood sample of an infected patient using the methods and primers described herein and known in the art.

The probes may be purified prior to use, using standard methods such as denaturing polyacrylamide gel electrophoresis, high performance liquid chromatography or gel filtration chromatography [see, e.g., Ausubel, et al., supra]. The probes of the invention may be used in any standard hybridization assay to detect the presence of *Plasmodium* in a sample. For example, Southern blot, dot blot, in situ hybridization (e.g., FISH), real-time hybridization detection by biosensors or dual probe, sandwich-type hybridization assays may be used [see, e.g., U.S. Pat. No. 5,519,127 and U.S. Pat. No. 5,629,156 (International Publication Number WO 94/10335), all of which are incorporated herein by reference]. These and other detection methods are well known to those of ordinary skill in the art. See, e.g., Short Protocols in Molecular Biology, Second Edition, F. M. Ausubel, Ed., all John Wiley & Sons, N.Y., editions as of 2008; Sambrook, et al., Molecular Cloning: A Laboratory Manual, 3.sup.rd ed., Cold Spring Harbor Laboratory Press, Cold Spring Harbor, 2001.

Alternatively, the probes may be used as primers in a polymerase chain reaction assay [see, e.g., Ausubel, et al., supra]. Biological samples that may be analyzed using the probes and methods of the invention include whole blood, CSF, bone marrow and tissue samples from, e.g., the spleen. Nucleic acid is extracted from the sample by standard methods (except in the case of in situ hybridization, where the cells are kept intact) and is analyzed using the probes in the assays listed above. A single probe or combinations of probes may be used in the assay.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G-C ratio within the nucleic acids. A single molecule that contains pairing of complementary nucleic acids within its structure is said to be "self-hybridized."

It is well known that numerous equivalent conditions may be employed to comprise suitable hybridization conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions and how to determine conditions, if necessary, that promote hybridization under conditions of high stringency (e.g., increasing the temperature of the hybridization and/or wash steps, the use of formamide in the hybridization solution, etc.).

The hybridization conditions used with the probes (e.g., in the methods of the invention) fall within the range of, for example, 30-50% formamide at 25° C.-42° C. or mixtures of GuSCN and formamide between 25-37° C. As is known by one of ordinary skill in the art, the selection of hybridization conditions depends on the length and nucleotide content (i.e., GC compared to AT) of the probe. Accordingly, hybridization conditions may be adjusted to accommodate these factors. In addition, the use of different salts (e.g., guanidine thiocyanate or guanidine hydrochoride compared with NaCl) and denaturing agents (e.g., NP-40, sodium dodecyl sulfate) may require adjustment of the salt concentration and the temperature, as can readily be determined by one skilled in the art. The adjustment of these and other parameters to achieve suitable hybridization conditions is known to one of ordinary skill in the art.

Non-limiting examples of hybridization conditions that may be used in the present invention are as follows. In Southern blot analysis, the following hybridization conditions may be used: 30% to 50% formamide in 2×SSC at 42° C. After hybridization, the filters are washed using standard methods. For example, three 15 minute post-hybridization washes at 25° C. in 2×SSC to 0.1×SSC and 0.1% SDS may be carried out in order to remove unbound probes. For RNA blots hybridizations in 30% formamide at room temperature overnight were performed. Excess probes were removed by washing three 15 min washes in 2×SSC with 0.1% SDS.

For in situ hybridization, the following conditions may be used as described in U.S. Pat. Nos. 6,165,723, 7,927,801 and U.S. Pat. No. 8,632,963 (which are herein incorporated by reference): GuSCN (1.5 to 3.5 M depending on the probe sequence) between room temperature and 37° C. or mixtures of GuSCN and formamide between room temperature and 37° C. for 30 minutes to one hour, followed by washes in SSC (2× to 0.1×) and 0.1% SDS.

EXEMPLIFICATION

Malaria Parasites, Other Human Pathogens and Uninfected Human Blood

Smears of *P. knowlesi* on pre-cleaned microscope slides for FISH assays were prepared from two different sources of the parasite viz. (1) frozen blood from a West Malaysian strain of *P. knowlesi* first isolated in 1962 from *M. fascicularis* and subsequently maintained by serial passage in monkeys (ATCC 30192 obtained from American Type Culture Collection or ATCC, Atlanta, Ga.) and (2) fresh in vitro cultures of the A1-H.1 clone, initially derived from the reference *P. knowlesi* H strain first isolated from a patient [Chin W, Contacos P G, Coatney G R, Kimball H R. A naturally acquited quotidian-type malaria in man transferable to monkeys. Science. 1965; 149:865] and then recently adapted to grow in vitro in human red blood cells [Moon R W, Hall J, Rangkuti F, Ho Y S, Almond N, Mitchell G H, et al. Adaptation of the genetically tractable malaria pathogen *Plasmodium knowlesi* to continuous culture in human erythrocytes. Proc Natl Acad Sci USA. 2013; 110:531-536. doi: 10.1073/pnas.1216457110], obtained at the London School of Hygiene and Tropical Medicine, London, UK. *Plasmodium falciparum, P. malariae* and *P. ovale* human blood smears were provided by the KEMRI/Walter Reed Project, Kisumu, Kenya, and *P. vivax* human blood smears by the Kasturba Medical College Hospital, Mangalore, India, all being derived from anonymized left over patient samples as previously described [Shah J, Mark O, Weltman H, Barcelo N, Lo W, Wronska D, et al. Fluorescence in situ hybridization (FISH) assays for diagnosing malaria in endemic areas. PLoS One. 2015; 10(9): e0136726].

Uninfected EDTA-treated human blood was obtained from ID-FISH Technology Inc., Palo Alto, Calif. Bacterial and protozoan blood-borne pathogens from different sources were used as additional specificity controls in the PK-FISH assay and these are detailed in Table 1.

TABLE 1

| Bacterial and Protozoan Pathogens as Additional Specificity Controls | |
|---|---|
| Pathogen | Source |
| Bacteria | |
| Anaplasma phagocytophilum | Prof. Stephen J. Dumler, John Hopkins University, Baltimore, MA |
| Borrelia burgdorferi | ATCC 35210-B31 |
| Bartonella henselae | ATCC 49882 |

TABLE 1-continued

Bacterial and Protozoan Pathogens as Additional Specificity Controls

| Pathogen | Source |
| --- | --- |
| Ehrlichia chaffeensis | Prof. Stephen J. Dumler, John Hopkins University, Baltimore, MA |
| Leptospira interrogans | ATCC 23476 |
| Protozoa | |
| Babesia microti | ATCC 30221 |
| Babesia duncani | ATCC PRA-302 |
| Trypanosoma cruzi | Dr. George L. Stewart, University of West Florida, Pensacola, FL. |
| Leishmania major amastigotes and promastigotes | Kenya Medical Research Institute, Nairobi, Kenya |

FISH Assay Reagents

Novel *Plasmodium knowlesi* probes were used in the study. Also used were *Plasmodium* genus-specific DNA probes, 4% formamide solution for smear preparation (other smear preparation solutions may be substituted as are known to one of ordinary skill in the art without undue experimentation), *Plasmodium* Wash Buffer, *Plasmodium* Rinse Buffer (1×PBS) and *Plasmodium* Counterstain (0.25 µg DAPI/ml in 50% glycerol) (ID-FISH Technology Inc., Palo Alto, Calif.). The use of the *Plasmodium* genus-specific probe to detect the four common human *Plasmodium* species and also *P. knowlesi* by FISH has been previously described [Shah J, Mark O, Weltman H, Barcelo N, Lo W, Wronska D, et al. Fluorescence in situ hybridization (FISH) assays for diagnosing malaria in endemic areas. PLoS One. 2015; 10(9): e0136726]. The novel *P. knowlesi*-specific probes used herein (SEQ ID NOs: 3, 4 and 5) are based on nucleotide sequences that are conserved in all 18S rRNA sequences of different *P. knowlesi* isolates from humans and macaques deposited to date in GenBank. The ID-FISH assay was performed according to the manufacturer's instructions provided except where formamide smear preparation treatment was omitted as specifically stated.

In the ID-FISH assay, the *P. knowlesi*-specific probe was labeled with Alexa 488 green fluorescent dye and the *Plasmodium* genus-specific probe with Atto 550 orange fluorescent dye. Therefore with LED illumination, *P. knowlesi* parasites are expected to appear green under the blue filter (excitation 492 nm; emission 530 nm) in the assay. Under the green filter (excitation 560; emission 630 nm), all *Plasmodium* species, including *P. knowlesi* are expected to appear orange.

Analytical Specificity of the *Plasmodium knowlesi* FISH Assay

Thin blood smears of *P. knowlesi* from monkey blood and in vitro culture in human blood, together with control smears from uninfected human blood, other human malaria parasite species derived from patients and the set of unrelated blood-borne pathogens were tested in the PK-FISH assay to assess its specificity for detecting *P. knowlesi*.

*Plasmodium knowlesi* infected monkey blood: This was done first at the ID-FISH laboratories, Palo Alto, Calif. in order to establish the *P. knowlesi* FISH assay procedure. EDTA-treated monkey blood containing parasites was mixed with 4% formamide 3 parts blood: 1 part formamide by volume. A set of four thin smears was prepared from each test sample. Each smear was prepared from 4 µl of the mixture, air-dried and fixed in methanol for subsequent testing in the PK-FISH assay. Briefly, after the addition of 12 µl of appropriate hybridization buffer containing the two probes to each methanol-fixed smear, the smear was covered with a plastic cover-slip and placed in a humid chamber at 37° C. for 15 min for hybridization. After 15 min, each smear was washed twice for 2 min each with 1× *Plasmodium* Wash Buffer at ambient temperature, followed by a rinse with 1× *Plasmodium* Rinse Buffer. After drying the smears in complete darkness, a drop of *Plasmodium* counterstain was added to each smear. The smear was then covered with a glass coverslip and viewed at ×1000 magnification, in an Olympus light microscope with an attached LED unit containing a blue-green filter set.

*Plasmodium knowlesi* grown in vitro in human blood: A1-H.1 parasites (a human-adapted laboratory line derived from the *P. knowlesi* H strain known to one of ordinary skill in the art) from a culture at 5% parasitemia were used to prepare thin blood smears without the use of the formamide for smear preparation and then fixed in methanol at the London School of Hygiene and Tropical Medicine and subsequently analyzed by FISH assay at the ID-FISH laboratories, Palo Alto, Calif. as described above for macaque blood.

Control *Plasmodium* species, uninfected human blood and unrelated pathogens: Smears were prepared utilizing formamide for smear preparation treatment and then tested with a FISH assay at the ID-FISH laboratories, Palo Alto, Calif. as described above for macaque blood.

Analytical Sensitivity as the Limit of Detection (LOD) in the FISH Assay

In a manner previously described for *P. falciparum* and *P. vivax* [Shah J, Mark O, Wellman H, Barcelo N, Lo W, Wronska D, et al. Fluorescence in situ hybridization (FISH) assays for diagnosing malaria in endemic areas. PLoS One. 2015; 10(9): e0136726], the lowest concentration of parasites that could be detected in every one of the replicated smears at different serial dilutions of *P. knowlesi* from monkey blood or human blood culture was used to estimate the analytical sensitivity of the assay.

*Plasmodium knowlesi* in monkey blood: The parasitemia determined by Giemsa staining was 42,000 parasites per µl in the original monkey blood sample. This was serially diluted in EDTA-treated normal human venous blood (ID-FISH laboratories, Palo Alto, Calif.) at 1:5, 1:10, 1:50, 1:100, 1:500 and 1:1,000 dilutions. At each dilution multiple thin blood smears were made and three smears at each dilution were then tested in the PK-FISH assay. Based on the data, the greatest dilution at which parasites could be detected by the *P. knowlesi*-specific probe in all three replicate smears was considered to be the provisional limit of detection or LOD. Once a provisional LOD was determined, an additional 17 smears were tested at this dilution for confirming the LOD.

*Plasmodium knowlesi* grown in vitro in human blood: A1-11.1 culture at 3.9% parasitemia was diluted 1:10, 1:100 and subsequently at serial two-fold dilutions in EDTA-treated normal human blood at the London School of Hygiene and Tropical Medicine, London, UK to prepare smears for determining the LOD. Initially two smears at 1:200 and greater dilutions were tested to determine a provisional LOD where both duplicate smears were positive in the PK-FISH assay. Based on the provisional LOD, 20 replicate smears at the same dilution as well as two-fold higher and two-fold lower dilutions were made and transported for testing by the PK-FISH assay in the ID-FISH laboratories, Palo Alto, Calif. The greatest dilution at which all 20 replicate smears were positive in the assay was considered to be the LOD.

Analytical Specificity of the P. knowlesi FISH Assay

It was first shown that both the Plasmodium genus-specific probe and the P. knowlesi-specific probe in the PK FISH assay reacted with P. knowlesi from monkey blood as shown in FIG. 1 where photographs showing the fluorescence observed in the PK-FISH assay with the P. knowlesi-specific probe (green) and the Plasmodium genus-specific probe (orange) on monkey blood smears containing P. knowlesi. Fluorescence is seen in a single microscope field at ×1000 magnification using the two different filters is shown in each set of paired photographs. The four sets of paired photographs are from four different fields (i)-(iv).

Figure 2:
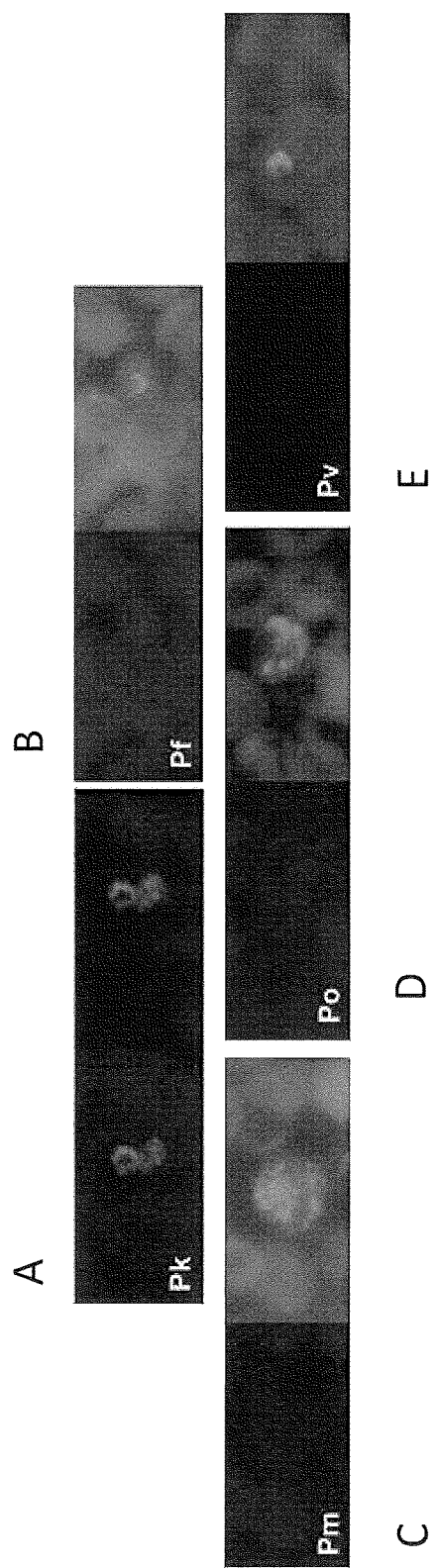
FIG. 2 (A-E) shows photographs showing the fluorescence observed in the PK-FISH assay with the *P. knowlesi*-specific probe (green; left) and the *Plasmodium* genus-specific probe (orange; right) in blood smears containing *P. knowlesi* (A; Pk), *P. falciparum* (B; Pf), *P. malariae* (C; Pm), *P. ovale* (D; Po) and *P. vivax* (E; Pv). Each set of paired photographs show the fluorescence in the same microscope field at ×1000 magnification using the two different filters.

Subsequent tests showed that the P. knowlesi-specific probe used in the PK-FISH assay did not react with P. falciparum, P. vivax, P. malariae or P. ovale that were however detected by the Plasmodium genus-specific probe (FIG. 2). Photographs showing the fluorescence observed in the PK-FISH assay with the P. knowlesi-specific probe (green; left) and the Plasmodium genus-specific probe (orange; right) in blood smears containing P. knowlesi (A; Pk), P. falciparum (B; Pf), P. malariae (C; Pm), P. ovale (D; Po) and P. vivax (E; Pv). Each set of paired photographs show the fluorescence in the same microscope field at ×1000 magnification using the two different filters.

Figure 3:
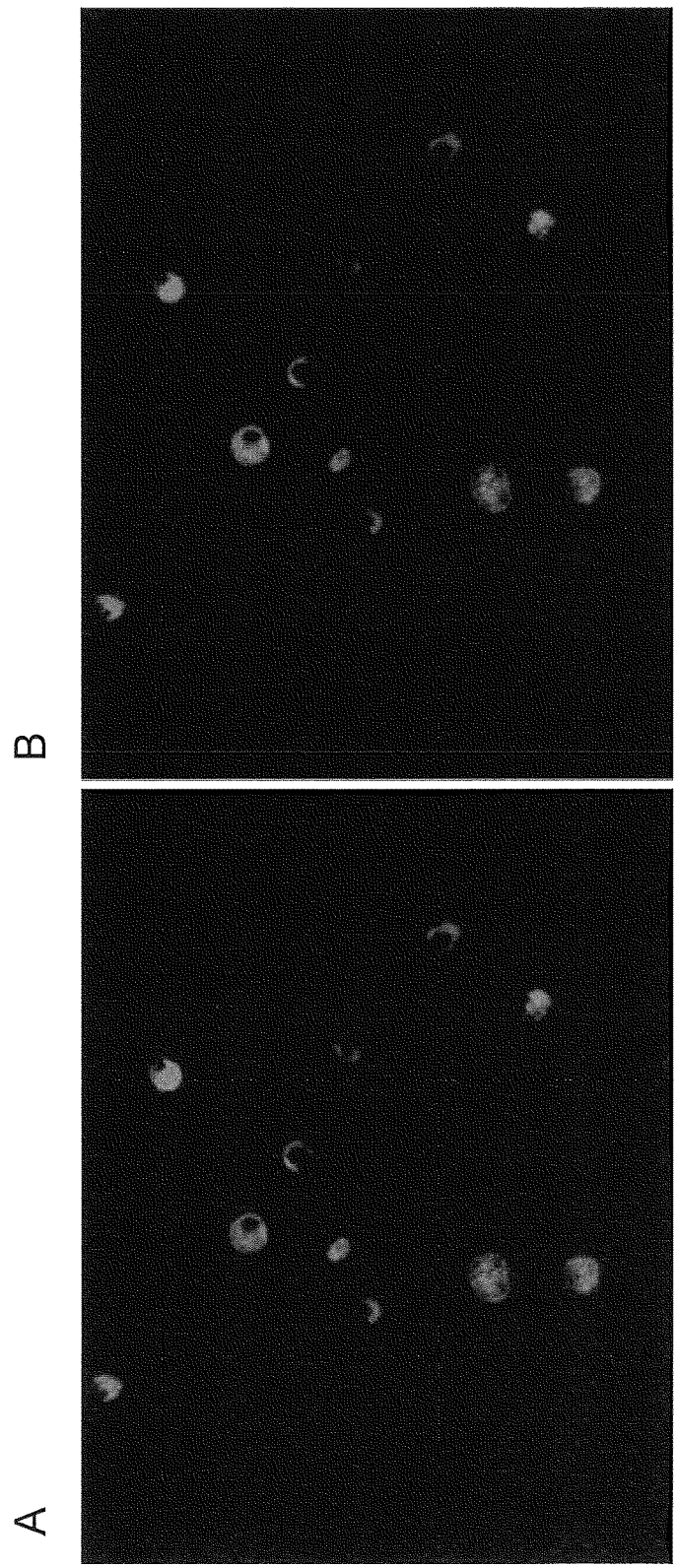
FIGS. 3 (A & B) shows photographs showing the fluorescence observed in the PK-FISH assay with the *P. knowlesi*-specific probe (A; green; left) and the *Plasmodium* genus-specific probe (B; orange; right) on *P. knowlesi* A1-H.1 cultured in human blood. Fluorescence seen in the same microscope field at ×1000 magnification using the two different filters is shown in the paired photographs.

Similarly, the A1-H.1 P. knowlesi human isolate grown in vitro in human blood was later shown to react positively with the Plasmodium genus-specific probe and the P. knowlesi-specific probe in the PK-FISH assay (FIG. 3). Photographs showing the fluorescence observed in the PK-FISH assay with the P. knowlesi-specific probe (A; green; left) and the Plasmodium genus-specific probe (B; orange; right) on P. knowlesi A1-H.1 cultured in human blood. Fluorescence seen in the same microscope field at ×1000 magnification using the two different filters is shown in the paired photographs. None of the other blood-borne bacterial and protozoan pathogens listed in Table 1 under Methods and Materials or uninfected human blood cells gave a positive reaction with either of the two probes in the PK-FISH assay.

Analytical Sensitivity of the P. knowlesi FISH Assay

The greatest dilution at which the monkey blood-derived P. knowlesi was detected in the PK-FISH assay in every one of the 20 replicate smears was 1:500. Based on the original parasitemia of 42,000 parasites per µl determined by Giemsa staining, this corresponded to a LOD of 84 P. knowlesi parasites per µl of blood.

The greatest dilution of the culture at which the in vitro grown P. knowlesi A1-H.1 could be detected in both duplicate smears in the PK-FISH assay was 1:6,400. This corresponds to a provisional LOD of 61 parasites per µl of blood. The LOD was confirmed with the 20 additional smears tested at 1:6,400 dilution as all smears were positive at this dilution. At a 1:3,200 dilution corresponding to 123 parasites per µl, all 20 replicate smears were also positive in the PK-FISH assay and this was also the case with the duplicate smears initially tested at this and lower dilutions. At 1:12,800 dilution corresponding to 31 parasites per µl, 16 of the 20 replicate smears were positive giving a detection rate of 80%. At 1:25,600 and greater dilutions of the culture, no parasites could be detected in either of the duplicate smears by the PK-FISH assay.

The LOD of P. knowlesi with the Plasmodium genus-specific probe observed under green filter was the same as that observed with the P. knowlesi-specific probe under the blue filter in both monkey blood and in vitro human red blood cell culture.

Plasmodium Genus 18S rRNA-Specific Probes

Plasmodium genus specific probes of the invention include probes PGenus1 and PGenus2, which have the sequences:

```
PGenus1
                                       (SEQ ID NO: 1)
    5'-TCTCGCTTGCGCGAATACTCG-3'

PGenus2
                                       (SEQ ID NO: 2)
    5'-CCAAAGACTTTGATTTCTCAT-3'
```

Plasmodium knowlesi 18S rRNA-Specific Probes

Plasmodium knowlesi specific probes of the invention include probes PK1, PK2 and PK3, which have the sequences:

```
PK1
                                       (SEQ ID NO: 3)
    5'-CGATACGCGGAGGCATCAGTTATGTGGATTTDTAGC-3'

PK2
                                       (SEQ ID NO: 4)
    5'-CGATACGCGGAGGTATCAGTTATGTGGATTTATAGC-3'

PK3
                                       (SEQ ID NO: 5)
    5'-CTAATCTCCGGAGAGAAAAGAAAAACTCTTATTTAAAA-3'
```

Table 2, below, shows results of the experiments described above using a combination of PK1 and PK2 probes. PK1 and PK2 were used in combination to ensure there was no cross reactivity with the P. falciparum, P. vivax, P. ovale and P. malariae conditions.

TABLE 2

| Whole blood Source | Parasite | Plasmodium Genus Probe (orange) | P. knowlesi Probe (green) |
|---|---|---|---|
| Human | P. falciparum | Positive | Negative |
| Human | P. vivax | Positive | Negative |
| Human | P. ovale | Positive | Negative |
| Human | P. malariae | Positive | Negative |
| Monkey (ATCC 30192)-M. fascicularis | P. knowlesi | Positive | Positive |
| Human | P. knowlesi H strain, | Positive | Positive |
| Human | Negative | Negative | Negative |

Equivalent experiments show that using one or more of the probes designated PK1, PK2 and PK3 (i.e., SEQ ID NO: 3, SEQ ID NO: 4 and SEQ ID NO: 5), singly or in combination, or complementary sequences thereof, produced results equivalent to those shown in Table 2.

From the above description, one skilled in the art can easily ascertain the essential characteristics of the present invention and, without departing from the spirit and scope thereof, can make various changes and modifications of the invention to adapt it to various usages and conditions. Thus, other embodiments are also within the claims.

---

SEQUENCE LISTING (1) GENERAL INFORMAll0N:
(iii) NUMBER OF SEQUENCES: 4

(2) INFORMATION FOR SEQ ID NO: 1:
(i) SEQUENCE CHARACTERISTICS:
(A) LENGTH: 21 base pairs

SEQUENCE LISTING (B) TYPE: nucleic acid
(C) STRANDEDNESS: single
(D) TOPOLOGY: linear
(ji) MOLECULE TYPE: DNA
(xi) SEQUENCE DESCRIPTION: SEQ ID NO:1:
TCTCGCTTGC GCGAATACTC G (3) INFORMATION FOR SEQ ID NO: 2:
(i) SEQUENCE CHARACTERISTICS:
(A) LENGTH: 21 base pairs
(B) TYPE: nucleic acid
(C) STRANDEDNESS: single
(D) TOPOLOGY: linear
(ji) MOLECULE TYPE: DNA
(xi) SEQUENCE DESCRIPTION: SEQ ID NO: 2:
CCAAAGACTT TGATTTCTCA T (3) INFORMATION FOR SEQ ID NO: 3:
(i) SEQUENCE CHARACTERISTICS:
(A) LENGTH: 36 base pairs
(B) TYPE: nucleic acid
(C) STRANDEDNESS: single
(D) TOPOLOGY: linear
(ji) MOLECULE TYPE: DNA (xi) SEQUENCE DESCRIPTION: SEQ ID NO: 3:
CGATACGCGG AGGCATCAGT TATGTGGATT TDTAGC (4) INFORMATION FOR SEQ ID NO: 4:
(i) SEQUENCE CHARACTERISTICS:
(A) LENGTH: 36 base pairs
(B) TYPE: nucleic acid
(C) STRANDEDNESS: single
(D) TOPOLOGY: linear
(ji) MOLECULE TYPE: DNA
(xi) SEQUENCE DESCRIPTION: SEQ ID NO: 4:
CGATACGCGG AGGTATCAGT TATGTGGATT TATAGC (5) INFORMATION FOR SEQ ID NO: 5:
(i) SEQUENCE CHARACTERISTICS:
(A) LENGTH: 39 base pairs
(B) TYPE: nucleic acid
(C) STRANDEDNESS: single
(D) TOPOLOGY: linear
(ji) MOLECULE TYPE: DNA
(xi) SEQUENCE DESCRIPTION: SEQ ID NO: 5:
CTAATCTCCG GAGAGAAAAG AAAAACTCTT ATTTTAAAA

---

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 1
tctcgcttgc gcgaatactc g                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ccaaagactt tgatttctca t                                              21

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cgatacgcgg aggcatcagt tatgtggatt tdtagc                              36

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence: Synthetic

```
        probe

<400> SEQUENCE: 4
cgatacgcgg aggtatcagt tatgtggatt tatagc                              36

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ctaatctccg gagagaaaag aaaaactctt attttaaaa                           39
```

We claim:

1. A method for detecting the presence of *Plasmodium knowlesi* in a sample, said method comprising the steps of:
   a) contacting said sample with a labeled nucleic acid probe suitable for detecting *Plasmodium knowlesi* in a hybridization assay, the probe consisting of a labeled nucleic acid sequence consisting of SEQ ID NO: 3 and/or SEQ ID NO: 4 and/or SEQ ID NO:5, or full-length complementary sequences thereof, under conditions that permit said probe to hybridize to *Plasmodium knowlesi* nucleic acid, wherein any said label is selected from one or more of radioisotopes, biotin, digoxigenin, fluorochromes, modified nucleotides and enzymes; and
   b) detecting said probe bound to said *Plasmodium knowlesi* nucleic acid in said sample as an indication of the presence of *Plasmodium knowlesi* in said sample.

2. The method of claim 1, wherein said labeled nucleic acid probe consists of labeled nucleic acid sequence consisting of SEQ ID NO: 3 or a full-length complementary sequence of SEQ ID NO: 3.

3. The method of claim 1, wherein said labeled nucleic acid probe consists of labeled nucleic acid sequence consisting of SEQ ID NO: 4 or a full-length complementary sequence of SEQ ID NO: 4.

4. The method of claim 1, wherein said labeled nucleic acid probe consists of labeled nucleic acid sequence consisting of SEQ ID NO: 5 or a full-length complementary sequence of SEQ ID NO: 5.

5. The method of claim 1 wherein said detecting comprises detecting probes bound to said *Plasmodium knowlesi* nucleic acid by Fluorescent in Situ Hybridization (FISH).

6. The method of claim 1 wherein said detecting comprises detecting probes bound to said *Plasmodium knowlesi* nucleic acid by a Dot Blot assay.

7. The method of claim 1 wherein the sample is selected from the group consisting of whole blood, cerebrospinal fluid (CSF), bone marrow and tissue sample.

8. The method of claim 7 wherein the tissue sample is isolated from a spleen.

9. A composition comprising one or more of a labeled nucleotide sequence consisting of SEQ ID NO: 3, a labeled sequence complementary to the nucleotide sequence consisting of SEQ ID NO: 3, a labeled nucleotide sequence consisting of SEQ ID NO: 4, a labeled sequence complementary to the nucleotide sequence consisting of SEQ ID NO: 4, a labeled nucleotide sequence consisting of SEQ ID NO: 5 and a labeled sequence complementary to the nucleotide sequence consisting of SEQ ID NO: 5, wherein any said label is selected from one or more of radioisotopes, biotin, diqoxigenin, fluorochromes, modified nucleotides and enzymes.

10. The composition of claim 9, wherein the labeled nucleotide sequence consists of a labeled nucleotide sequence consisting of SEQ ID NO: 3.

11. The composition of claim 9, wherein the labeled nucleotide sequence consists of a labeled sequence complementary to the nucleotide sequence consisting of SEQ ID NO: 3.

12. The composition of claim 9, wherein the labeled nucleotide sequence consists of a labeled nucleotide sequence consisting of SEQ ID NO: 4.

13. The composition of claim 9, wherein the labeled nucleotide sequence consists of a labeled sequence complementary to the nucleotide sequence consisting of SEQ ID NO: 4.

14. The composition of claim 9, wherein the labeled nucleotide sequence consists of a labeled nucleotide sequence consisting of SEQ ID NO: 5.

15. The composition of claim 9, wherein the labeled nucleotide sequence consists of a labeled sequence complementary to the nucleotide sequence consisting of SEQ ID NO: 5.

* * * * *